United States Patent [19]

Mörsdorf et al.

[11] Patent Number: 6,130,218

[45] Date of Patent: Oct. 10, 2000

[54] POLYMORPHIC FORM OF DOXAZOSIN MESYLATE (FORM I)

[75] Inventors: Johann Peter Mörsdorf, Langenzenn; Ingomar Grafe, Nürnberg, both of Germany

[73] Assignee: Heumann Pharma GmbH, Nuremberg, Germany

[21] Appl. No.: 08/992,252

[22] Filed: Dec. 17, 1997

[30] Foreign Application Priority Data

Dec. 20, 1996 [EP] European Pat. Off. ............... 96120601

[51] Int. Cl.[7] ....................... C07D 407/14; A61K 31/517
[52] U.S. Cl. ............................................. 514/253; 544/291
[58] Field of Search .................... 514/260, 253; 544/291

[56] References Cited

U.S. PATENT DOCUMENTS

| | | | |
|---|---|---|---|
| 2,699,054 | 1/1955 | Conover | 260/559 |
| 4,092,315 | 5/1978 | Bianco | 544/291 |
| 4,188,390 | 2/1980 | Campbell | 424/251 |
| 4,251,532 | 2/1981 | Roteman | 424/251 |
| 4,816,455 | 3/1989 | Schickaneder et al. | 514/254 |
| 5,294,615 | 3/1994 | Meyer et al. | 514/254 |
| 5,412,095 | 5/1995 | Morley et al. | 544/291 |
| 5,504,207 | 4/1996 | Mannino et al. | 544/291 |

FOREIGN PATENT DOCUMENTS

| | | |
|---|---|---|
| 0459666 | 12/1991 | European Pat. Off. . |
| 94/09783 | 5/1994 | WIPO . |

OTHER PUBLICATIONS

Greman et al, *Farm. vestn.*, 48, p. 292 (1997).
Xu Liying et al, *Chinese Journal of Medicinal Chemistry*, vol. 5, No. 4, p. 266 (1995).
*The Merck Index*, eleventh edition, Merck & Co., Inc., Rahway, New Jersey, p. 539 (1989).
*USAN and the USP Dictionary of Drug Names*, Mack Printing Company, Easton, Pennsylvania, p. 197 (1998).
The Merck Index, 1996, Merck & Co., Inc. Whitehouse Station, N.J., XP002030968, #3489: Doxazosin.
Greman et al., Chemical Abstracts, vol. 128, entry 7263 (1997).

*Primary Examiner*—John M. Ford
*Attorney, Agent, or Firm*—Burns, Doane, Swecker & Mathis, L.L.P.

[57] ABSTRACT

A new crystalline and anhydrous form of doxazosin mesylate is described. The new form is crystalline and anhydrous and is characterized in its X-ray spectrum by the following reflex positions of high and medium intensity: 15.40°, 16.85°, 18.06°, 24.15° and 25.81°. Owing to its crystalline properties, the new form of doxazosin mesylate according to the invention has surprising advantages both with regard to its synthesis and for pharmaceutical processing into solid dosage forms. A process for preparing the new form of doxazosin mesylate and pharmaceutical compositions comprising the new form of doxazosin mesylate are also described.

17 Claims, 2 Drawing Sheets

DTA Spectrum of Form I
of Doxazosin Mesylate according to the Invention

POLYMORPHIC FORM OF DOXAZOSIN MESYLATE (FORM I)

CROSS-REFERENCE TO COMPANION APPLICATIONS

Copending applications Ser. No. 08/992,251 [Attorney Docket No. 015200-047] and No. 08/992,474 [Attorney Docket No. 015200-048], filed concurrently herewith and assigned to the Assignee hereof.

BACKGROUND OF THE INVENTION

1. Technical Field of the Invention

This invention relates to a new crystalline and anhydrous form of doxazosin mesylate, a process for its preparation and pharmaceutical compositions comprising this new Form I.

2. Description of the Prior Art 1-(4-Amino-6,7-dimethoxy-2-quinazolinyl)-4-[(2,3-dihydro-1,4-benzodioxin-2-yl)carbonyl]piperazine mono methanesulfonate, the INN name of which is doxazosin mesylate, is a diaminoquinazolyl derivative of the class of the $\alpha_1$-receptor blockers.

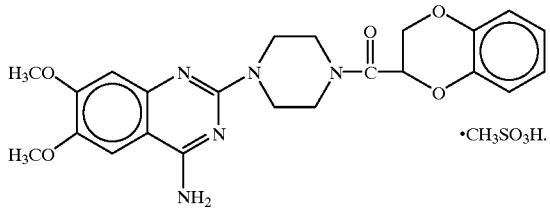

It shows a great structural similarity to the older representatives of this class, prazosin hydrochloride and terazosin hydrochloride. Whereas the two latter active substances are used primarily only in the treatment of high blood pressure, in the case of doxazosin mesylate, there is an additional indication, namely, the treatment of benign prostate hyperplasia.

Unlike prazosin and terazosin, doxazosin is used therapeutically not as the hydrochloride but as the mesylate, that is, as a salt of methanesulfonic acid.

Although medicaments containing doxazosin mesylate are already on the market, doxazosin mesylate has not hitherto been described. Even U.S. Pat. No. 4,188,390, which discloses doxazosin for the first time, does not contain a description of doxazosin mesylate. Only doxazosin monohydrochloride is described in the examples in that publication.

Because of its extremely sparing solubility in water, however, the hydrochloride is unsuitable for pharmaceutical purposes.

Attempts to prepare doxazosin mesylate in the conventional ways prove to be very difficult and lead to unsatisfactory results. On the one hand, doxazosin base is sparingly soluble in the solvents commonly used for forming salts. It is sufficiently soluble only in polar, aprotic, high-boiling solvents such as, for example, dimethylformamide. In these solvents, however, the solubility of doxazosin mesylate is similar to that of the base, so that the yields of mesylate obtained are totally unsatisfactory. Moreover, from the pharmacological aspect, dimethylformamide is a critical residual solvent in medicinally active substances. The current ICH guideline for residual solvents in pharmaceutical active substances ("ICH Guideline: Residual Solvents," Pharmeuropa, Vol. 8, No. 1, page 103, March 1996) places dimethylformamide in Class 2 as a solvent having known toxicity and limits the permissible residual content of the solvent to 500 ppm.

On the other hand, a second standard method for forming salts also fails because of the particular properties of doxazosin base and its salts. Doxazosin base can be dissolved in weak acids such as, for example, acetic acid, and in this phase can be subjected to clarification filtration for the removal of insoluble foreign particles which is indispensable for a pharmaceutical active substance, and afterwards the mesylate can be precipitated by adding methanesulfonic acid or a salt of methanesulfonic acid. When this procedure is carried out at room temperature, however, an unfilterable gel is obtained. If the procedure is carried out at more elevated temperatures, for example 50° C., this gel agglomerates or, in higher concentrations, separates out as a second, non-solidifying oily phase. Through the addition of organic solvents such as, for example, acetone, the suction capacity of the precipitated doxazosin mesylate can be improved. However, drying of this product leads to the formation of lumps owing to the high moisture content, and impurities from the mother liquor, in particular coloring impurities, are included therein. Ultimately, a form of doxazosin mesylate is obtained which is shown by the X-ray spectrum to be amorphous and is moreover hygroscopic. Thermal analysis reveals an exothermic transformation at 200° C. before the substance melts with decomposition at 267° C.

SUMMARY OF THE INVENTION

This invention is therefore based on the object of providing a crystalline and anhydrous form of doxazosin mesylate which, owing to its physical properties, in particular its crystalline properties and its behavior in water, is easy to handle both during its chemical preparation and during pharmaceutical formulation.

This object is fulfilled according to the invention by a new crystalline and anhydrous form of doxazosin mesylate, which is referred to below as Form I.

This invention accordingly provides Form I of doxazosin mesylate, which shows an X-ray powder diagram having the following reflex positions of high and medium intensity: 15.40°, 16.85°, 18.06°, 24.15° and 25.81°, and which is crystalline and anhydrous.

DETAILED DESCRIPTION OF BEST MODE AND SPECIFIC/PREFERRED EMBODIMENTS OF THE INVENTION

Figure 1:
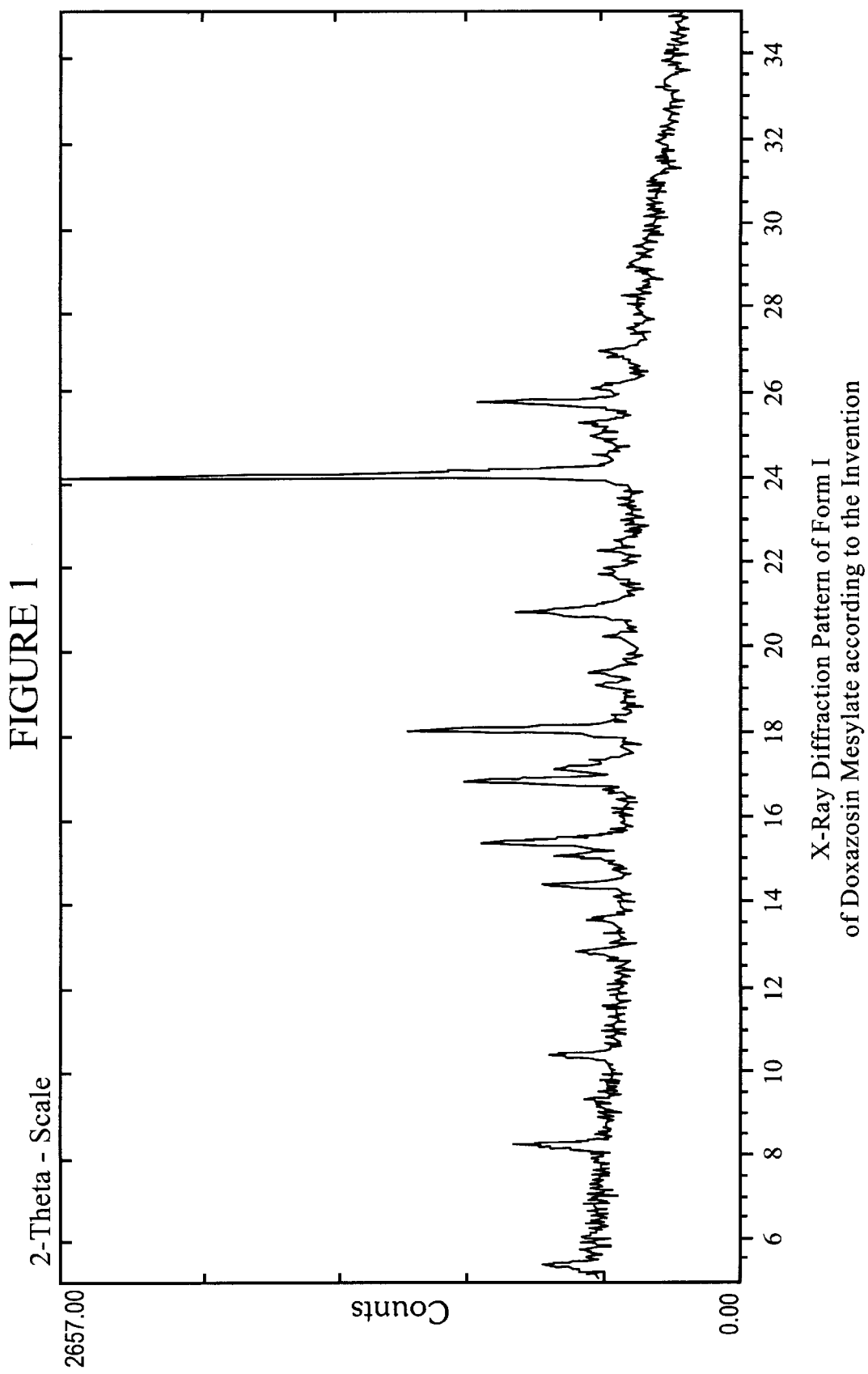
FIG. 1 is an X-ray diffraction pattern of Form I doxazosin mesylate in accord with the invention.

Form I according to the invention has the characteristic X-ray diffraction pattern as shown in FIG. 1, measured with the use of Cu-K$_{\alpha 1}$ radiation and of a Ge monochromator having a spacing of 0.017° within the diffraction angle range 2 θ of 5° to 35°, and reflex positions of high and medium intensity at 15.40°, 16.85°, 18.06°, 24.15° and 25.81°.

Form I of doxazosin mesylate according to the invention differs from the other forms of doxazosin mesylate in a number of other properties over and above the X-ray diffraction pattern. These properties can therefore also be used to distinguish it from the other forms.

Figure 2:
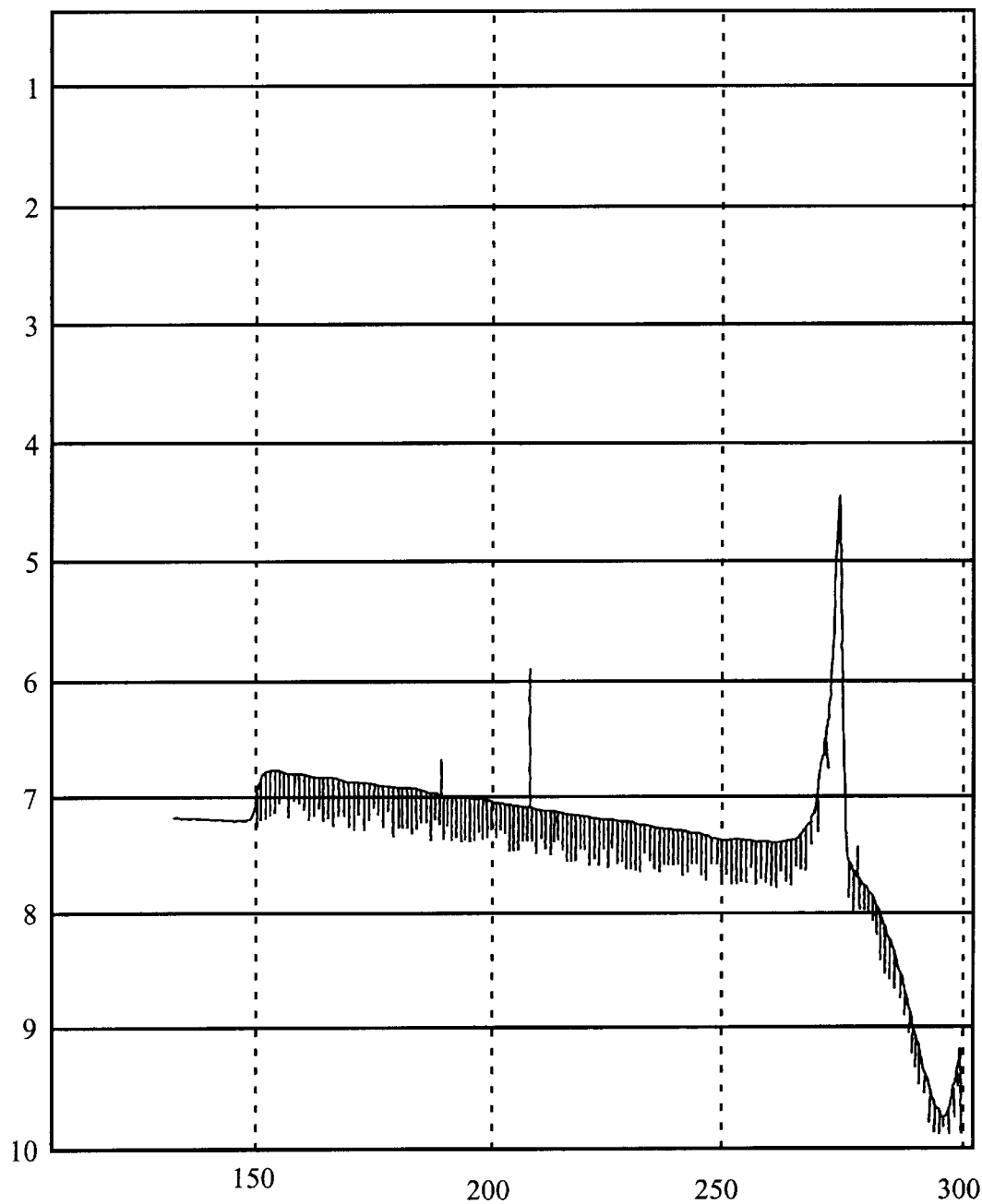
FIG. 2 is a DTA spectrum of Form I doxazosin mesylate in accord with the invention.

Form I of doxazosin mesylate can be further characterized with the aid of differential thermal analysis (DTA). From the DTA spectrum of Form I measured in the range of 150° C. to 300° C., which is shown in FIG. 2, Form I is characterized by a single endothermic peak at 275° C., which corresponds to the melting point of Form I.

The invention also provides a process for preparing the above Form I of doxazosin mesylate according to the invention, which comprises:

(1) suspending doxazosin base in an alcohol-water mixture;

(2) converting the base, by the addition thereto of a weak acid, into the soluble salt of the weak acid;

(3) adding methanesulfonic acid and adjusting the pH value to a value within the range of from about 2 to about 4 by adding a base, to precipitate doxazosin mesylate;

and (4) recovering the precipitated doxazosin mesylate, optionally after stirring and cooling, by filtration, washing with an organic solvent and drying.

In the first step of the process according to the invention, doxazosin base is suspended in an alcohol-water mixture. Examples of suitable alcohols are lower alkyl alcohols, such as methanol, ethanol or n-butanol, as well as alkyl glycols such as lower alkyl glycols, for example, methyl glycols. In the alcohol-water mixture, the volume ratio of alcohol: water is advantageously from about 95:5 to about 50:50, preferably from about 80:20 to about 90:10. The suspension is preferably effected with stirring and at a temperature of from about 40° C. up to the reflux temperature of the alcohol-water mixture used.

In the second step of the process according to the invention, the base is converted, by the addition thereto of a weak acid, into the soluble salt of the weak acid. Examples of weak acids are formic acid, acetic acid or lactic acid. Preferably, an excess quantity of the weak acid (up to about five times) is added to the doxazosin base.

In the third step of the process according to the invention, doxazosin mesylate is precipitated by adding methanesulfonic acid and by adjusting the pH value to a value within the range of from about 2 to about 4 by adding a base. The ratio of doxazosin base to methanesulfonic acid is within the range of from about 1:1 to about 1:1.1 and is preferably substantially equimolar. Methanesulfonic acid is preferably used in the form of a 70% aqueous solution. The pH value is adjusted to a value within the range of from about 2 to about 4, preferably of from about 2.5 to about 3, by adding a base, preferably of concentrated ammonia solution. The reaction temperature in this step is from about 20°C. to about 60° C., preferably from about 20° C. to about 40° C.

Adherence to the pH range specified above is essential, in order to prevent, on the one hand, a hydrolysis of the carbonamide group of the doxazosin and, on the other hand, a coprecipitation of the doxazosin base.

In the final step of the process according to the invention, the precipitated doxazosin mesylate, optionally after stirring and cooling, is recovered by filtration, washing with an organic solvent and drying. The precipitated doxazosin mesylate is preferably stirred for from about 4 to about 8 hours, preferably about 6 hours, at a temperature of from about 20° C. to about 60° C., preferably about 40° C. Prior to the filtration, which is preferably carried out under suction, the mixture is optionally cooled to a temperature of from about 10° C. to about 30° C., preferably about 20° C. The product obtained is washed with an organic solvent, preferably with a lower alkyl alcohol such as methanol, and dried in a vacuum.

Owing to its crystalline properties, Form I of doxazosin mesylate according to the invention has surprising advantages both with regard to its synthesis and the purity of the product and for its pharmaceutical processing into solid dosage forms. As described above, the forms of doxazosin mesylate prepared in the conventional ways are obtained in the form of gel-like precipitates which even in the presence of organic solvents are very voluminous, contain large quantities of mother liquor and therefore have moisture contents and drying losses respectively of up to 50%. Because of this, impurities, in particular coloring impurities, are included in or adsorbed onto the dried product. In addition, the gel-like voluminous product leads to extremely long filtration and centrifugation times, which are very disadvantageous from the procedural point of view.

In comparison, Form I according to the invention is obtained as a colorless solid substance which forms good crystals and can be filtered and centrifuged without difficulty. Adhering mother liquor can be removed without difficulty by washing the filter cake with a suitable solvent, so that a product of high purity is obtained.

Amorphous solids, and hygroscopic solids even more so, cannot be processed at all satisfactorily into pharmaceuticals as, for example, they have low bulk densities and poor flow properties. Moreover, special operating techniques and devices are necessary for the handling of hygroscopic solids, in order to obtain reproducible results, for example, relating to the content of active ingredients or the stability in the final medicament produced.

Form I of doxazosin mesylate according to the invention can be used therapeutically in the same way as the doxazosin base and its pharmaceutically acceptable acid addition salts, and as the doxazosin mesylate having unknown morphological properties which is available on the market. The main areas of indication of the present Form I are the treatment of high blood pressure and the treatment of benign prostate hyperplasia.

The invention therefore further provides a pharmaceutical composition or medicament which, in addition to one or more conventional auxiliary substances and/or carriers, comprises Form I of doxazosin mesylate.

Thus, Form I of doxazosin mesylate according to the invention can be formulated into the conventional forms of administration, including peroral and parenteral forms of administration. Tablets or capsules are preferred formulations. They can be produced by conventional mixing processes and with the use of conventional auxiliary substances and carriers, as well as binders, disintegrants, flavorings and the like. The dose corresponds to that of the existing forms of doxazosin salts.

In order to further illustrate the present invention and the advantages thereof, the following specific example is given, it being understood that same is intended only as illustrative and in nowise limitative.

EXAMPLE

Production of Form I of Doxazosin Mesylate According to the Invention 112.5 g doxazosin base is dissolved at 60° C. in a mixture of 140 ml water and 500 ml n-butanol by adding approx. 33 ml 85% formic acid. 27 ml methanesulfonic acid (70%) is subsequently added slowly to the solution. This is then adjusted to a pH value of 3 by adding concentrated ammonia solution.

At 40° C. a fine precipitate settles which, after having been stirred for approximately 6 hours at 40° C. and cooled to 20° C., is filtered off under suction.

After the product has been washed with methanol and dried in a vacuum, 116 g (85% of theoretical yield) of a colorless solid of Form I is obtained, which has the X-ray diffraction pattern shown in FIG. 1 and the DTA spectrum shown in FIG. 2.

While the invention has been described in terms of various preferred embodiments, the person skilled in this art will appreciate that various modifications, substitutions, omissions and changes can be made without departing from the spirit thereof. Accordingly, it is intended that the scope of the present invention be limited solely by the scope of the following claims, including equivalents thereof.

What is claimed is:

1. The polymorphic form of 1-(4-amino-6,7-dimethoxy-2-quinazolinyl)-4-[(2,3-dihydro-1,4-benzodioxin-2-yl) carbonyl]piperazine monomethanesulfonate which is crystalline and anhydrous and is characterized by an X-ray powder diffraction pattern having reflex positions of high and medium intensity at 15.40°, 16.85°, 18.06°, 24.15° and 25.81°.

2. A process for preparing the polymorphic form of 1-(4-ammo-6,7-dimethoxy-2-quinazolinyl-4-[(2 3-dihydro-1, 4-benzodioxin-2-yl)carbonyl]piperazine monomethanesulfonate which is crystalline and anhydrous and is characterized by an X-ray powder diffraction pattern having reflex positions of high and medium intensity at 15.40°, 16.85°, 18.06°, 24.15° and 25.81°, said process comprising;

(1) suspending the base 1-(4-amino-6,7-dimethoxy-2-quinazolinyl)-4-[(2,3-dihydro-1,4-benzodioxin-2-yl) carbonyl]piperazine in an alcohol-water mixture;

(2) adding a weak acid to convert said base into the soluble salt of said weak acid;

(3) adding methanesulfonic acid and adjusting the pH value to a value within the range of from about 2 to about 4 by adding a base, to precipitate the desired polymorphic form of 1-(4-amino-6,7-dimethoxy-2-quinazolinyl-4-[(2,3-dihydro-1,4-benzodioxin-2-yl) carbonyl]piperazine monomethanesulfonate; and (4) recovering the precipitated desired polymorphic form of 1-(4-amino-6,7-dimethoxy-2-quinazolinyl-4-[(2,3-dihydro-1,4-benzodioxin-2-yl)carbonyl]piperazine monomethanesulfonate, optionally after stirring and cooling, by filtration, washing with an organic solvent and drying.

3. A process according to claim 2, wherein the alcohol used in step (1) is a lower alkyl alcohol.

4. A process according to claim 3, wherein the lower alkyl alcohol is n-butanol.

5. A process according to claim 2, wherein the alcohol used in step (1) is a lower alkyl glycol.

6. A process according to claim 2, wherein in the alcohol-water mixture, the volume ratio of alcohol:water is from about 95:5 to about 50:50.

7. A process according to claim 6, wherein the volume ratio of alcohol:water is from about 80:20 to about 90:10.

8. A process according to claim 2, wherein the weak acid used in step (2) is formic acid, acetic acid or lactic acid.

9. A process according to claim 8, wherein the weak acid is formic acid.

10. A process according to claim 2, wherein the pH value in step (3) is adjusted to a value of from about 2.5 to about 3.

11. A process according to claim 10, wherein the pH is adjusted using concentrated ammonia solution.

12. A process according to claim 2, wherein the organic solvent used in step (4) is a lower alkyl alcohol.

13. A process according to claim 12, wherein the lower alkyl alcohol is methanol.

14. A pharmaceutical composition comprising, in solid dosage form:

(a) an effective antihypertensive amount of the polymorphic form of 1-(4-amino-6,7-dimethoxy-2-quinazolinyl)-4-[(2,3-dihydro-1,4-benzodioxin-2-yl) carbonyl]piperazine monomethanesulfonate which is crystalline and anhydrous and is characterized by an X-ray powder diffraction pattern having reflex positions of high and medium intensity at 15.40°, 16.85°, 18.06°, 24.15° and 25.81°; and (b) a non-toxic, pharmaceutically acceptable carrier therefor.

15. A composition according to claim 14, formulated for peroral administration.

16. A composition according to claim 1, in tablet or capsule form.

17. A method for the treatment of high blood pressure in a warm-blooded animal in need of same, said method comprising administering to said animal an effective antihypertensive amount of the polymorphic form of 1-(4-amino-6,7-dimethoxy-2-quinazolinyl)-4-[(2,3-dihydro-1,4-benzodioxin-2-yl)carbonyl]piperazine monomethanesulfonate which is crystalline and anhydrous and is characterized by an X-ray powder diffraction pattern having reflex positions of high and medium intensity at 15.40°, 16.85°, 18.06°, 24.15° and 25.81°.

* * * * *